(12) United States Patent
Bosma et al.

(10) Patent No.: US 8,992,865 B2
(45) Date of Patent: Mar. 31, 2015

(54) SEALING DEVICE FOR USE IN A CARTRIDGE FOR MEDICAL DIAGNOSTICS

(71) Applicant: Biocartis SA, Lausanne (CH)

(72) Inventors: Rob Bosma, Sterksel (NL); Ronald De Gier, Eindhoven (NL)

(73) Assignee: Biocartis NV, Mechelen (BE)

( * ) Notice: Subject to any disclaimer, the term of this patent is extended or adjusted under 35 U.S.C. 154(b) by 0 days.

(21) Appl. No.: 14/344,646

(22) PCT Filed: Sep. 27, 2012

(86) PCT No.: PCT/EP2012/069142
§ 371 (c)(1),
(2) Date: Mar. 13, 2014

(87) PCT Pub. No.: WO2013/045587
PCT Pub. Date: Apr. 4, 2013

(65) Prior Publication Data
US 2014/0271410 A1    Sep. 18, 2014

(30) Foreign Application Priority Data
Sep. 28, 2011    (EP) .................................... 11183127

(51) Int. Cl.
*B01L 3/00*    (2006.01)
*A61B 10/00*    (2006.01)

(52) U.S. Cl.
CPC ............ *B01L 3/508* (2013.01); *A61B 10/0096* (2013.01); *B01L 3/502* (2013.01); *B01L 3/5023* (2013.01);
(Continued)

(58) Field of Classification Search
CPC ................................................ B01L 2300/045
USPC ............. 422/402, 411, 554, 939, 940; 435/36
See application file for complete search history.

(56) References Cited

U.S. PATENT DOCUMENTS

| 7,611,669 B1 | 11/2009 | Crisanti et al. ................... 422/57 |
| 2008/0118397 A1 | 5/2008 | Slowey et al. ................... 422/60 |

FOREIGN PATENT DOCUMENTS

| DE | 2 453 743 | 4/2009 | ............ G01N 33/50 |
| EP | 1 374 989 | 1/2004 | ............... B01J 19/00 |

(Continued)

OTHER PUBLICATIONS

International Search Report for International Application No. PCT/EP2012/069142, Dec. 10, 2012.

*Primary Examiner* — Jill Warden
*Assistant Examiner* — Matthew Krcha
(74) *Attorney, Agent, or Firm* — Kusner & Jaffe

(57) ABSTRACT

The present invention relates to a sealing device for closing an introduction aperture, the sealing device comprising a fixed support and a shutter mounted movably in translation relative to the support between an extended position and a final retracted position, wherein the sealing device is in a final retracted configuration and wherein the shutter closes introduction aperture. The device includes locking means for preventing any movement of the shutter when it is in the final retracted position. The sealing device further comprises an intermediate retracted configuration, wherein the shutter is at least partly retracted. The sealing device also comprises motion guiding means for guiding the movement of the shutter and designed so that the extension of the shutter is required to move the shutter from the intermediate retracted position to the final retracted position.

15 Claims, 2 Drawing Sheets

(52) U.S. Cl.
CPC .... *B01L 2200/025* (2013.01); *B01L 2200/0689* (2013.01); *B01L 2200/141* (2013.01); *B01L 2300/045* (2013.01); *B01L 2300/069* (2013.01); *Y10S 435/975* (2013.01); *Y10S 435/81* (2013.01)
USPC ........... 422/554; 422/402; 422/411; 422/430; 422/939; 422/940; 435/975; 435/810

(56) References Cited

FOREIGN PATENT DOCUMENTS

| | | | |
|---|---|---|---|
| EP | 2 229 888 | 9/2010 | ............. A61B 5/154 |
| WO | WO 2007/004103 | 1/2007 | ................ B01L 3/00 |
| WO | WO 2010/109445 | 9/2010 | ................ B01L 3/00 |
| WO | WO 2010/127464 | 11/2010 | ................ B01L 3/00 |
| WO | WO 2011/075667 | 6/2011 | ............. B01F 13/00 | ered cartridge for automated medical diagnostics, as described in WO 2007/004103, has proved to be a promising yet simple and practical solution. Such a cartridge usually contains all necessary equipment and reagents to run said diagnostic assays on a biological sample. The equipment in particular comprises various reagent compartments and a preparation chamber wherein a sample to be analyzed can be introduced and contacted with said reagents contained in the compartments. To allow the introduction of the biological sample in the preparation chamber, the latter usually comprises an introduction aperture through which the biological sample can be introduced by the user via a swab.

SEALING DEVICE FOR USE IN A CARTRIDGE FOR MEDICAL DIAGNOSTICS

FIELD OF THE INVENTION

The present invention relates to a sealing device for use in a cartridge.

BACKGROUND OF THE INVENTION

Advanced biotechnology research is nowadays focusing on multiplexed biological assays, which require high reproducibility and reliability. Recently, a cartridge for automated medical diagnostics, as described in WO 2007/004103, has proved to be a promising yet simple and practical solution. Such a cartridge usually contains all necessary equipment and reagents to run said diagnostic assays on a biological sample. The equipment in particular comprises various reagent compartments and a preparation chamber wherein a sample to be analyzed can be introduced and contacted with said reagents contained in the compartments. To allow the introduction of the biological sample in the preparation chamber, the latter usually comprises an introduction aperture through which the biological sample can be introduced by the user via a swab.

Preferably, the introduction aperture must be sealed once the biological sample has been introduced in the preparation chamber in order to avoid leakages and/or contaminations. Usually, a closure device is designated to insure a tamper-proof sealing of the preparation chamber during and/or after the diagnostic assays, meaning that the preparation chamber cannot be reopened by the user under normal use conditions. Thus, this prevents any direct contamination of the user or of the biological material contained in the preparation chamber and vice-versa. A cartridge that is sealed in such a tamper-proof manner will also ensure that the introduction opening will not be untimely reopened while the assay is running, which would invalidate the result of the biological assays due to possible contaminations of the preparation chamber.

A typical closure device existing in the art comprises a support and a closure element mounted movably in translation relative to the support between an extended position and a retracted position wherein the closure device is in a retracted configuration and wherein the closure element closes said aperture. The typical closure device further includes locking means for preventing movement of, the closure element once the latter is placed in the retracted position.

A cartridge equipped with this closure device presents however disadvantages:

The classical closure device may close untimely before the introduction of a biological sample which could render the cartridge unusable. One will understand that a user may easily and inadvertently close the introduction aperture by simply pushing the closure element prior to introducing the biological sample. The untimely closure may also occur during the packaging and/or transport of the cartridge.

The present invention aims to remedy all or part of the disadvantages mentioned above.

SUMMARY OF THE INVENTION

The present invention fulfills these objectives and provides a sealing device for closing an introduction aperture, the sealing device comprising a fixed support and a shutter mounted movably in translation relative to the support between an extended position and a final retracted position, wherein when the shutter is in said final retracted position the sealing device is in a final retracted configuration and the shutter closes said introduction aperture, the device further including locking means for preventing any movement of the shutter when it is in the final retracted position, the sealing device being characterized in that it comprises an intermediate retracted configuration, wherein the shutter is at least partly retracted when the sealing device is in said intermediate retracted position, the sealing device being further characterized in that it comprises motion guiding means for guiding the movement of the shutter and designated so that the extension of the shutter is required to move the shutter from, the intermediate retracted position to the final retracted position Thus, the sealing device according to the present invention comprises an intermediate retracted position and motion guiding means to prevent the untimely closure. It is advantageous to store or carry a cartridge equipped with the sealing device according to the invention placed in its intermediate configuration. Said motion guiding means prevent the move of the shutter from the intermediate retracted position to the final retracted position by a direct thrust. The motion guiding means are such that they impose the shutter to be moved from the intermediate retracted position to the final retracted position by a motion that comprises its extension from the intermediate retracted position to an extended position. Then, once extended, the shutter can be retracted towards the final retracted position. Thus, a user cannot move inadvertently the shutter from the intermediate retracted position to the final retracted position by a simple pushing motion on the shutter. The fact that the shutter must first be moved to an extended position before being retracted implies an intentional action of the user.

According to an embodiment of the present invention, the sealing device comprises switching means designed to shunt the movement of the shutter, when the shutter is being extended, so as to prevent the return of the shutter in the intermediate configuration. Advantageously, the switching means are designed to prevent the return in the intermediate retracted position when the shutter has been extended beyond a switching position. The switching means prevent the user from pushing the shutter back into the intermediate retracted position, when it has been extended beyond the switching position. Thus, the user does not have to worry about whether the shutter has been pushed back in the final retracted position and not in the first retracted position.

According to an embodiment of the present invention, the sealing device further comprises retaining means designed to prevent the extension of the shutter beyond the extended position.

In a preferred embodiment, the retaining means comprise a second limit stop. The retaining means prevent the separation of the shutter from the fixed support. The limit stop allows maintaining the shutter and the support assembled together and thus avoids the operator having to reinsert the extended shutter in the fixed support.

According to an embodiment of the present invention, the motion guiding means comprise at least a guide-pin, at least a deformable tongue and at least a guide groove cooperating together. Advantageously, the switching means comprise a deformable tongue and a first guide groove, said first guide groove being designated to cause an elastic deformation of said tongue in a third switching portion of said first guide groove comprising said switching position.

According to a possibility of the invention the sealing device comprises cutting means designed to cut a swab inserted in the introduction aperture when the shutter is moved towards the final retracted position. Thus, the cutting means allow the user to work safely and minimize the contamination of the swab comprising the sample, as the cutting means cut automatically the swab. Advantageously, the cutting means comprise at least a cutting edge mounted in a cutting slot and lying in the plane of the second plate of the shutter.

According to an embodiment of the present invention, the shutter and/or the support comprise or are made of polycarbonate.

According to an embodiment of the present invention, the shutter closes the introduction aperture when the sealing device is in the intermediate retracted configuration. Thus, the shutter ensure optimal storage conditions of the cartridge and in particular helps maintain a conditioned atmosphere during the storage and prevents the introduction of contaminants in the cartridge before the introduction of the biological sample.

The present invention also relates to a cartridge for performing medical assays comprising a sealing device according to the present invention.

The present invention is further illustrated by the following detailed description set forth in view of the appended drawings, which represent an exemplary and explanatory embodiment of a sealing device not restrictive of the invention, wherein:

DETAILED DESCRIPTION OF THE INVENTION

In order to avoid leakages and contaminations, a sealing device according to the present invention is designed to close an introduction aperture 1 provided in a diagnostic cartridge for introducing a biological sample. The sealing device comprises a fixed support 2, shown in the FIG. 1, and a shutter 3, shown in the FIG. 2, designed to be movably mounted in translation on the fixed support 2. The sealing device further comprises motion guiding means, designed to guide the movement of the shutter 3 on the fixed support 2 when the shutter 3 is being extended.

Figure 1:
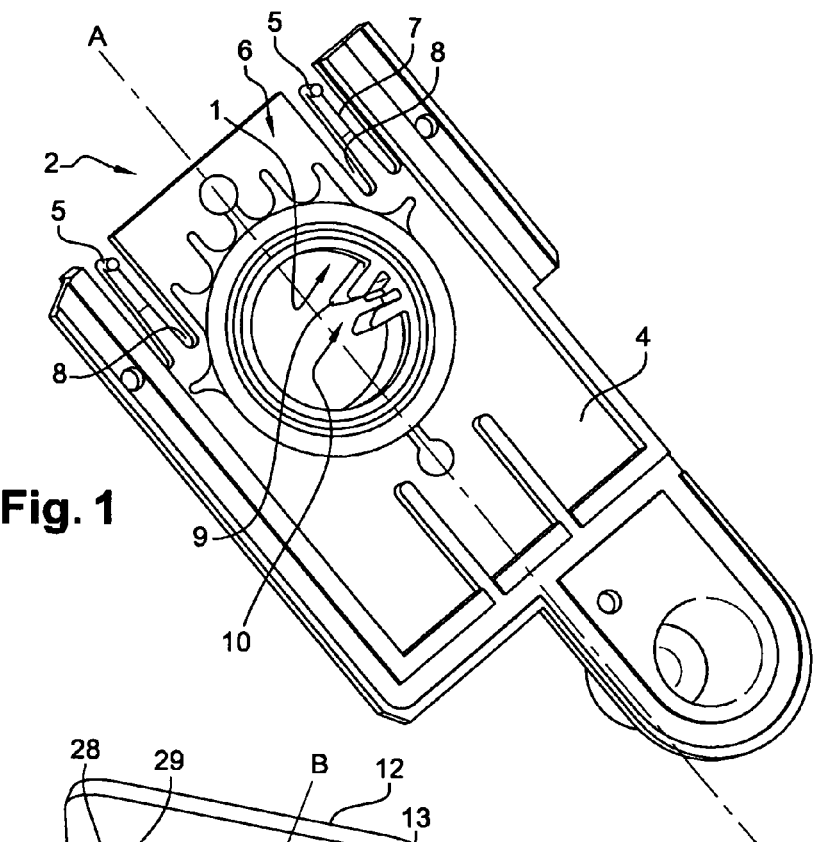
FIG. 1 illustrates a bottom perspective view of the fixed support according to the present invention.

The fixed support 2, illustrated in the FIG. 1, comprises a first plate 4 having a substantially rectangular shape and delineating the introduction aperture 1. The first plate 4 is provided with two cylindrical guide-pins 5 at one of its ends that corresponds to the width of the plate 4. The two guide-pins 5 are symmetrically located with respect to the longitudinal axis of the first plate 4 and extend in a direction substantially perpendicular to the plane of the first plate 4, so as to protrude from a first contacting side 6 of said first plate 4. The guide-pins 5 are respectively located at the end of two tongues 7 which are elastically deformable. Each tongue 7 is positioned in a slot 8 of the first plate 4 and extends in a direction substantially parallel to the longitudinal axis A of said first plate 4. Advantageously the first plate 4 comprises at least two tips 9 elastically deformable located on the edge of the insertion aperture 1, said tips 9 defining a gap 10 between them adapted to pinch a swab.

Figure 2:
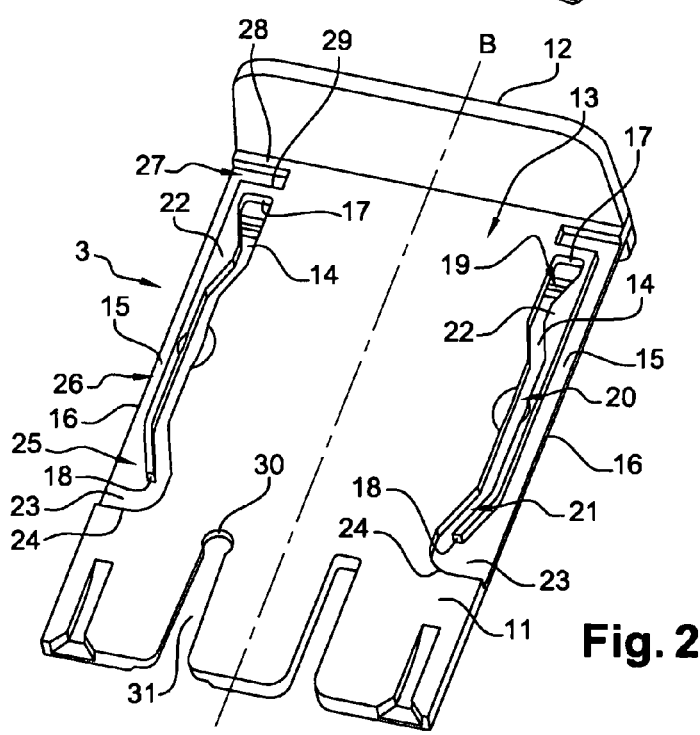
FIG. 2 illustrates a top perspective view of the closure device according to the present invention.

The shutter 3, shown in the FIG. 2, comprises a second plate 11 substantially rectangular and designed to cover totally or partially the insertion aperture 1, depending of the relative positions of the shutter 3 and the fixed support 2. The shutter 3 further comprises a prehension handle 12 substantially rectangular in shape and which length corresponds substantially to the width of the second plate 11. The prehension handle 12 extends substantially perpendicularly from one of the edges defining the width of the second plate 11, and is intended to be grasped by the user and is intended to enable the user to move the shutter 3. The second plate 11 of the shutter 3 comprises on a second contacting side 13 two pairs of guide grooves, each pair comprising a first guide groove 14 and a second guide groove 15. Each first and second guide groove 14, 15 extends in a direction substantially parallel to the longitudinal axis B, shown in FIG. 2, of the second plate 11 and is disposed along an edge 16 forming the length of the shutter 3. Each first guide groove 14 extends between a first limit stop 17, located near the prehension handle 12, and a switching position 18 distant from the prehension handle 12. The first guide groove 14 comprises three portions 19, 20, 21 which extend successively from the first limit stop 17 to the switching position 18. The said first portion 19 comprises at one of its end the first limit stop 17 and is curved in such a way to form a boss 22. The second portion 20, substantially straight, is followed by a third switching portion 21 extending to the switching position 18. The third switching portion 21 is curved towards the longitudinal axis B of the second plate 11. The third switching portion 21 opens onto a linking area 23. The linking area 23 comprises advantageously retaining means formed by a second limit stop 24 arranged facing the switching position 18. Each second guide groove 15 comprises three parts 25, 26, 27 of guide groove which extend successively from the switching position 18 towards the prehension handle 12. The first part 25 is curved toward the prehension handle 12 and towards the nearest edge forming the length of the second plate 11. The second part 26 extends the first part 25 and is substantially straight, extending between the nearest edge 16 of the second plate 11 and the first guide groove 14. The second portion 20 and the second part 26 of a given guide groove pair, are substantially parallel to each other. The third part 27 forms an extension of the second part 26 and extends perpendicularly to the longitudinal axis B of the second plate 11, between the first limit stop 17 of the first guide groove 14 and the prehension handle 12. Walls of the third part 27 form a second and third limit stop 28, 29. Advantageously, the shutter 3 further comprises cutting means. The cutting means comprises a cutting edge 30 disposed in a cutting slot 31 located at the opposite end of the prehension handle 12. The cutting edge 30 lies in the plane of the second plate 11 of the shutter 3.

The motion guiding means of the sealing device comprise the cylindrical guide-pins 5, the tongues 7 and the first and second guide grooves 14, 15.

The motion guiding means are designed so that the shutter 3 is moved along a first path between the intermediate retracted position and the extended position and along a second path between the extended position and the final retracted position. The switching means induce an elastic deformation of at least a part of the motion guiding means during the switching from the first path to the second path.

The shutter 3 and the support 2 are made of polycarbonate.

Figure 3:
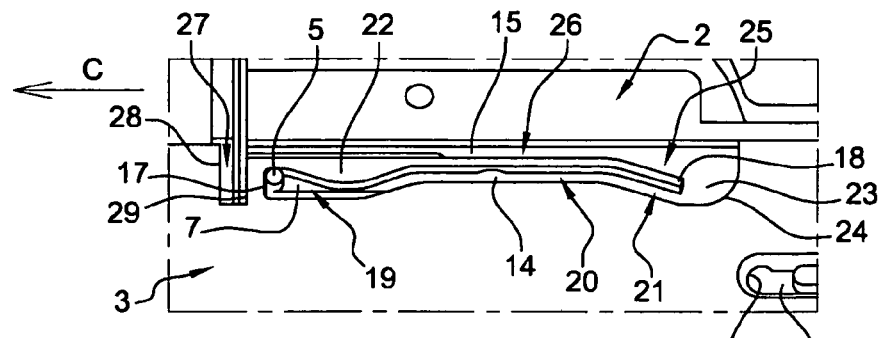
FIG. 3 illustrates a partial bottom perspective view of the sealing device in the intermediate retracted configuration.
Figure 4:
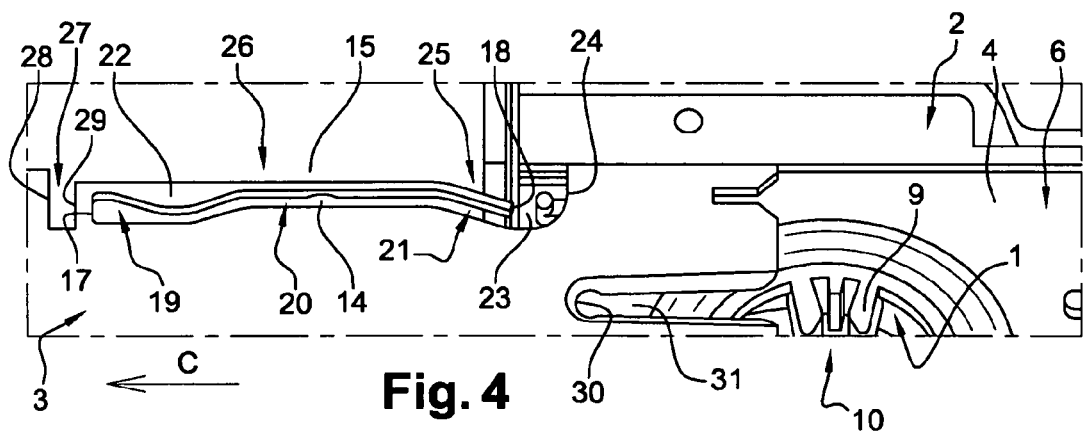
FIG. 4 illustrates a view similar to the FIG. 3 wherein the sealing device is in the extended configuration.
Figure 5:
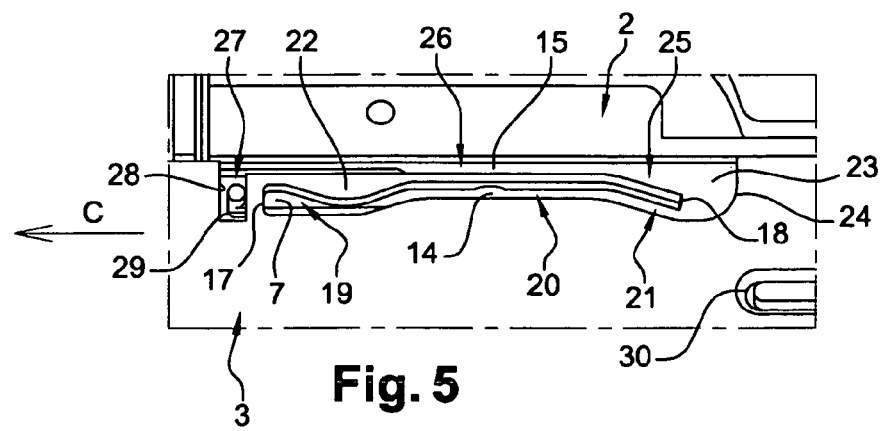
FIG. 5 illustrates a view similar to the FIG. 3 wherein the sealing device is in the final retracted configuration.

In working order, the shutter 3 is mounted on the fixed support 2 so that the first contacting side 6 of the fixed support 2 is positioned facing the second contacting side 13 of the shutter 3, so that each guide-pin 5 is inserted in a first guide groove 14. When the guide-pins 5 are in contact with a first limit stop 17, the sealing device is in an intermediate retracted configuration as shown in the FIG. 3. The displacement of the shutter 3 by the operator induces the movement of each guide-pin 5 in a first guide groove 14 and/or in a second guide groove 15. Each first limit stop 17 blocks guide-pins 5 and prevents the operator from pushing the shutter 3 in the direction opposite to the direction indicated by the arrow C shown in the FIGS. 3 to 5. From the intermediate retracted position and in order to open the insertion aperture 1, the operator has to pull the shutter 3 to move the guide-pins 5 along the first portion 19 of the guide groove 14, in the direction indicated by the arrow C. The boss 22 is designed to prevent the movement of the guide-pins 5 without the intervention of the operator. Indeed, the orientation and the form of the boss 22 as well as the form and orientation of the tongues 7 are chosen in order to require the deformation of the tongues 7, therefore requiring the operator to increase its effort while pulling the shutter 3 from the intermediate retracted position. When the operator continues to pull the shutter 3 in the direction indicated by the arrow C, the guide-pins 5 come out into the second portion 20 of the first guide groove 14. The operator, when continuing to pull the shutter 3, further induces the displacement of the guide-pins 5 from the second portion 20 to the third switching portion 21. The form of the third switching portion 21 and the movement of the guide-pins 5 in the third switching portion 21 bring the guide-pins 5 closer to the longitudinal axis A of the plate 11 and induce a deformation of the tongues 7, when the shutter 3 is displaced and until the guide-pins 5 arrive in the switching position 18. The movement of the guide-pins 5 in the first portion 19, in the second portion 20 and in the third switching position 18 is possible in the direction indicated by the arrow C or in the in the opposite direction. When the guide-pins 5 are moved in the direction indicated by the arrow C, beyond the switching position 18, the guide-pins 5 come out into the linking area 23 and the tongues 7 spring back to their initial form immediately after the switching position 18 is gone past. The initial form of the tongues 7 is chosen in such a way that each guide-pin 5 is facing the first part 25 of the second guide groove 15, in the linking area 23, when the tongues 7 are not bent. Immediately after the switching position is gone past when the guide-pins 5 are moved in the direction indicated by the arrow C, the sealing device is in the deployed configuration as shown in the FIG. 4. The guide-pins 5 can be moved within the linking area 23 in the direction indicated by the arrow C or in the opposite direction. Advantageously, the second limit stop 24 of the linking area 23 blocks the guide-pins 5 and prevents the operator from pulling the shutter 3 further and prevents from moving the guide-pins 5 beyond the linking area 23. Thus, the shutter 3 cannot be disassembled from the fixed support 2 by pulling it. In the extended position, the operator may insert through the insertion aperture 1 of the sealing device a swab comprising a biological sample to be analyzed. To proceed to do the assays on the sample in the proper conditions, the shutter 3 must be locked. The operator must therefore push the shutter 3 in the direction opposite to the direction indicated by the arrow C. In doing so, the operator leads the cylindrical guide-pins 5 to leave the linking area 23 and to enter the second guide groove 15 past the switching position 18. Indeed, considering the form of the tongues 7 and the forms of the guide groove 14, 15, the guide-pins 5 cannot enter the third switching portion 21 of the first guide groove 14. The first part 25 is curved and forces the operator to increase its effort while pushing the shutter 3 in the direction opposite to the direction indicated by the arrow C as the guide-pins 5 move along the first part 25 and the tongues 7 are being bent. The movement of the cylindrical guide-pins 5 in the first and second parts 26, 27 is possible in the direction indicated by the arrow C as well as in the opposite direction. The form of the tongues 7 and the forms and positions of the first and second parts 25, 26 are chosen so that the tongues 7 are bent when the guide-pins 5 are in the first and second parts 25, 26. When the operator continues to push the shutter 3, the guide-pins 5 enter the third part 27 which causes the tongues to spring back to their initial form immediately. When the guide-pins 5 are in the third part 27, the second and third limit stop 28, 29 form locking means and block the guide-pins 5 in order to prevent the shutter 3 from being moved. In this configuration, the sealing device is in the final retracted configuration as shown in the FIG. 5. The sealing device in the final retracted position is locked and cannot be deployed, preventing from contaminations and leaks during the biological assays. Advantageously, when the swab is inserted inside the insertion aperture 1 and maintained by the tips 9, the cutting means are designated so that the swab is introduced inside the cutting slot 31 in order to be cut by the cutting edge 30 during the movement of the shutter 3 towards the final retracted position.

Other embodiments of the invention will be apparent to those skilled in the art from consideration of the specification and practice of the invention disclosed herein. It is intended that the specification and example be considered as exemplary only, with the true scope and spirit of the invention being indicated by the following claims.

The invention claimed is:

1. A sealing device for use in a diagnostic cartridge, the sealing device comprising:
    a fixed support providing an introduction aperture of the diagnostic cartridge,
    a shutter mounted movably in translation relative to the fixed support, said shutter movable between an intermediate position, an extended position and a final retracted position,
    wherein when the shutter is in said intermediate position the sealing device is in an at least partly retracted configuration, and when the shutter is in said final retracted position the sealing device is in a final retracted configuration and the shutter closes said introduction aperture
    locking means for preventing any movement of the shutter when it is in the final retracted position,
    and
    motion guiding means for guiding the movement of the shutter wherein movement of the shutter to the extended position is required in order to move the shutter from the intermediate retracted position to the final retracted position.

2. Sealing device according to claim 1, wherein said sealing device further comprises switching means to shunt movement of the shutter when the shutter is being moved from the intermediate retracted position to the extended position, so as to prevent the return of the shutter to the intermediate retracted position.

3. Sealing device according to claim 2, wherein the switching means prevent the return of the shutter to the intermediate retracted position when the shutter has been extended beyond a switching position.

4. Sealing device according to claim 1, wherein said sealing device further comprises retaining means for preventing extension of the shutter beyond the extended position.

5. Sealing device according to claim 1, wherein said sealing device further comprises cutting means for cutting a swab inserted in the introduction aperture when the shutter is moved towards the final retracted position.

6. Sealing device according to claim 1, wherein the shutter and/or the support are comprised of polycarbonate.

7. Sealing device according to claim 1, wherein the shutter closes the introduction aperture when the shutter is in the intermediate retracted position.

8. A cartridge for performing assays on a sample comprising:
 a preparation chamber for receiving the sample; and
 a sealing device for closing an introduction aperture to the preparation chamber, the sealing device comprising:
 a fixed support providing an introduction aperture,
 a shutter mounted movably in translation relative to the fixed support, said shutter movable between an intermediate position, an extended position and a final retracted position, wherein when the shutter is in said intermediate position the sealing device is in an at least partly retracted configuration, and when the shutter is in said final retracted position the sealing device is in a final retracted configuration and the shutter closes said introduction aperture
 locking means for preventing any movement of the shutter when it is in the final retracted position,
 and
 motion guiding means for guiding movement of the shutter wherein movement of the shutter to the extended position is required in order to move the shutter from the intermediate retracted position to the final retracted position.

9. A sealing device for use in a diagnostic cartridge, the sealing device comprising:
 a fixed support providing an introduction aperture of the diagnostic cartridge,
 a shutter mounted movably in translation relative to the fixed support, said shutter movable between an intermediate position, an extended position and a final retracted position, wherein when the shutter is in said intermediate position the sealing device is in an at least partly retracted configuration, and when the shutter is in said final retracted position the sealing device is in a final retracted configuration and the shutter closes said introduction aperture,
 locking means for preventing any movement of the shutter when it is in the final retracted position, and
 a guide element comprised of at least a guide-pin, at least a deformable tongue, and at least a guide groove cooperating together, said guide element guiding movement of the shutter, wherein movement of the shutter to the extended position is required in order to move the shutter from the intermediate retracted position to the final retracted position.

10. A sealing device for use in a diagnostic cartridge, the sealing device comprising:
 a fixed support providing an introduction aperture of the diagnostic cartridge,
 a shutter mounted movably in translation relative to the fixed support, said shutter movable between an intermediate position, an extended position and a final retracted position, wherein when the shutter is in said intermediate position the sealing device is in an at least partly retracted configuration, and when the shutter is in said final retracted position the sealing device is in a final retracted configuration and the shutter closes said introduction aperture,
 locking means for preventing any movement of the shutter when it is in the final retracted position,
 motion guiding means for guiding movement of the shutter, wherein movement of the shutter to the extended position is required in order to move the shutter from the intermediate retracted position to the final retracted position, and
 a switching element comprised of a deformable tongue and a first guide groove, wherein said switching element shunts movement of the shutter when the shutter is being moved from the intermediate retracted position to the extended position, so as to prevent the return of the shutter to the intermediate retracted position.

11. Sealing device according to claim 10, wherein said switching element prevents the return of the shutter to the intermediate retracted position when the shutter has been extended beyond a switching position.

12. Sealing device according to claim 11, wherein said first guide groove causes an elastic deformation of said tongue in a switching portion of said first guide groove comprising said switching position.

13. A sealing device for use in a diagnostic cartridge, the sealing device comprising:
 a fixed support providing an introduction aperture of the diagnostic cartridge,
 a shutter mounted movably in translation relative to the fixed support, said shutter movable between an intermediate position, an extended position and a final retracted position, wherein when the shutter is in said intermediate position the sealing device is in an at least partly retracted configuration, and when the shutter is in said final retracted position the sealing device is in a final retracted configuration and the shutter closes said introduction aperture,
 locking means for preventing any movement of the shutter when it is in the final retracted position,
 motion guiding means for guiding movement of the shutter, wherein movement of the shutter to the extended position is required in order to move the shutter from the intermediate retracted position to the final retracted position, and
 a limit stop for preventing extension of the shutter beyond the extended position.

14. A sealing device for use in a diagnostic cartridge, the sealing device comprising:
 a fixed support providing an introduction aperture of the diagnostic cartridge,
 a shutter mounted movably in translation relative to the fixed support, said shutter movable between an intermediate position, an extended position and a final retracted position, wherein when the shutter is in said intermediate position the sealing device is in an at least partly retracted configuration, and when the shutter is in said final retracted position the sealing device is in a final retracted configuration and the shutter closes said introduction aperture,
 locking means for preventing any movement of the shutter when it is in the final retracted position,
 motion guiding means for guiding movement of the shutter, wherein movement of the shutter to the extended position is required in order to move the shutter from the intermediate retracted position to the final retracted position, and
 a cutting element having a cutting edge to cut a swab inserted in the introduction aperture when the shutter is moved towards the final retracted position.

15. Sealing device according to claim 14, wherein said cutting edge is mounted in a cutting slot and lies in a plane of a plate of the shutter.

* * * * *